US012685841B2

(12) United States Patent　　　　(10) Patent No.:　US 12,685,841 B2
　　　Koarashi　　　　　　　　　　　(45) Date of Patent:　　　Jul. 21, 2026

(54) FIXING STRUCTURE FOR INSERTING MEMBER

(71) Applicant: HI-LEX CORPORATION, Takarazuka (JP)

(72) Inventor: Shinsaku Koarashi, Takarazuka (JP)

(73) Assignee: HI-LEX CORPORATION, Hyogo (JP)

( * ) Notice: Subject to any disclaimer, the term of this patent is extended or adjusted under 35 U.S.C. 154(b) by 612 days.

(21) Appl. No.: 18/250,187

(22) PCT Filed: Oct. 21, 2021

(86) PCT No.: PCT/JP2021/038861
　　§ 371 (c)(1),
　　(2) Date: Apr. 21, 2023

(87) PCT Pub. No.: WO2022/085748
　　PCT Pub. Date: Apr. 28, 2022

(65) Prior Publication Data
　　US 2024/0001082 A1　　Jan. 4, 2024

(30) Foreign Application Priority Data

Oct. 22, 2020　(JP) ................................. 2020-177550

(51) Int. Cl.
　　*A61M 25/02*　　　　(2006.01)
　　*F16J 15/32*　　　　(2016.01)
(52) U.S. Cl.
　　CPC .............. *A61M 25/02* (2013.01); *F16J 15/32* (2013.01)
(58) Field of Classification Search
　　CPC ...... A61M 25/0285; A61M 2025/0286; A61M 2025/024
　　See application file for complete search history.

(56) References Cited

U.S. PATENT DOCUMENTS

| | | | |
|---|---|---|---|
| 4,546,987 | A | 10/1985 | Bucher |
| 2019/0290887 | A1 | 9/2019 | Ayuzawa |

(Continued)

FOREIGN PATENT DOCUMENTS

| | | |
|---|---|---|
| JP | S614092 U | 2/1986 |
| JP | H03254758 A | 11/1991 |

(Continued)

OTHER PUBLICATIONS

English Translation of JP-2017104437.*

(Continued)

*Primary Examiner* — Courtney B Fredrickson
(74) *Attorney, Agent, or Firm* — Renner, Otto, Boisselle & Sklar, LLP

(57)　　　　　　ABSTRACT

A fixing structure comprises a driveline, a fixing member, through which the driveline is inserted, and a holding mechanism to hold the driveline. The holding mechanism comprises a chuck member to grasp the driveline, a sealing member, and a screw member to press the chuck member and the sealing member. The sealing member has a main body portion, and an annular protruding portion projecting from an end of the main body portion, wherein a cross-sectional shape of the annular protruding portion gradually decreases in diameter toward the projecting direction. The annular protruding portion is configured to be bent and deformed to the inner side of the sealing member in the radial direction by contacting an end face of the chuck member.

4 Claims, 8 Drawing Sheets

(56)     References Cited

U.S. PATENT DOCUMENTS

| | | |
|---|---|---|
| 2021/0370024 A1 | 12/2021 | Koarashi |
| 2021/0402150 A1 | 12/2021 | Koarashi |
| 2022/0211978 A1 | 7/2022 | Koarashi |

FOREIGN PATENT DOCUMENTS

| | | | | |
|---|---|---|---|---|
| JP | 2017104437 | A | * | 6/2017 |
| JP | 2019166310 | A | | 10/2019 |
| WO | 2020085274 | A1 | | 4/2020 |
| WO | 2020111183 | A1 | | 6/2020 |
| WO | 2020230681 | A1 | | 11/2020 |

OTHER PUBLICATIONS

International Search Report for priority international application No. PCT/JP2021/038861, mailed on Dec. 7, 2021.

Office Action issued in corresponding Indian Application No. 202317035055 dated Jun. 3, 2026.

* cited by examiner

FIXING STRUCTURE FOR INSERTING MEMBER

This application is a national phase of International Application No. PCT/JP2021/038861, filed Oct. 21, 2021, which claims priority to Japanese Application No. 2020-177550, filed Oct. 22, 2020, each of which is hereby incorporated herein by reference in its entirety.

TECHNICAL FIELD

The present invention relates to a fixing structure for an inserting member.

BACKGROUND ART

Conventionally, a fixing structure to hold an inserting member to be inserted through a target and to be fixed to the target is known.

For example, as one example thereof, Patent document 1 discloses a set for retaining a percutaneous catheter having a percutaneous terminal (a fixing member) having a through passage (an insertion hole), a catheter (an inserting member) to be inserted through the through passage, and a cap (a screw member) being formed to be screw-fitted to the head of the percutaneous terminal to press an annular rubber elastic body (a sealing member) disposed in the surroundings of a fixing site of the catheter to fix the catheter.

PRIOR ART DOCUMENT

Patent Document

Patent Document 1: JP H03-254758 A

SUMMARY OF THE INVENTION

Problem to be Solved by the Invention

Incidentally, in a common annular sealing member such as an O ring and the like, to increase dose contactability such as airtightness and liquid-tightness, the inner diameter thereof needs to be set in advance to be slightly smaller compared to the outer diameter of a target member to which sealing function is applied so as to be mounted in the surroundings (on the outer side in the radial direction) of the above-mentioned target member.

Here, in a fixing structure for inserting a medical tube as an inserting member such as a skin button for use in an artificial heart, a connector portion having an outer diameter being sufficiently greater than an outer diameter of the inserting member is provided at the tip of the inserting member on a side in which the inserting member is exposed to the outer side of the body. Therefore, it is difficult to pass the connector portion through the common sealing member as described above, and it is very difficult to arrange a sealing member at a predetermined location of the fixing structure.

On the other hand, as a solution for such a problem, it can be considered that the sealing member is configured in a long cylindrical shape having the inner diameter being sufficiently greater compared to the outer diameter of the connector portion, and, after the sealing member is arranged at a predetermined location of the fixing structure, the sealing member is compressed in the axial direction to elastically deform the inner peripheral surface inwardly in the radial direction, for example. However, it is impractical since the structure as an overall fixing structure becomes complicated and also the external shape becomes excessive.

An object of the present invention is to provide a compact fixing structure for an inserting member, which has a sealing member that can easily pass through a member (for example, a connector portion) being provided to an inserting member and having an outer diameter being sufficiently greater than an outer diameter of the inserting member and that can secure a sufficient close contactability with respect to the inserting member.

Means to Solve the Problem

A problem to be solved by the present invention is as described above and next a means to solve this problem will be described.

In other words, a fixing structure for an inserting member according to the present invention is a fixing structure for an inserting member, comprising: the inserting member to be inserted through a target; a fixing member fixed to the target and having an insertion hole through which the inserting member is inserted; and a holding mechanism to hold the inserting member with respect to the fixing member, wherein the fixing member has a female screw portion on one end of the insertion hole in an axial direction and has a fixing member-side fitted portion, wherein a cross-sectional shape of the fixing member-side fitted portion gradually decreases in diameter from one end side toward an other end side in an intermediate portion in the axial direction, the holding mechanism comprises a chuck member having a chuck member-side first fitting portion having a shape corresponding to the fixing member-side fitted portion, wherein the chuck member grasps the inserting member by fitting the chuck member-side first fitting portion to the fixing member-side fitted portion between an outer peripheral surface of the inserting member and an inner peripheral surface of the insertion hole, a sealing member configured by a cylindrical elastic member and being arranged on one end side in the axial direction with respect to the chuck member, and a screw member arranged on one end side in the axial direction with respect to the sealing member, wherein the screw member has a male screw portion to be screwed into the female screw portion, and the screw member is configured to press the chuck member and the sealing member toward the other end side in the axial direction by screwing the male screw portion into the female screw portion; the sealing member has a main body portion through which the inserting member is inserted, and an annular protruding portion projecting toward the other end side in the axial direction from an end on the other end side of the main body portion, wherein a cross-sectional shape of the annular protruding portion gradually decreases in diameter toward a projecting direction of the annular protruding portion, the annular protruding portion is configured to be bent and deformed to the inner side of the sealing member in a radial direction by contacting the annular protruding portion with an end face of the chuck member on one end side in the axial direction

Effects of the Invention

As the effects of the present invention, the effects as shown below will be achieved.

In other words, according to the present invention of a fixing structure for an inserting member, it is possible to realize a compact fixing structure for an inserting member, which fixing structure has a sealing member that can easily pass through a member (for example, a connector portion) being provided to an inserting member and having an outer diameter being sufficiently greater than an outer diameter of the inserting member and that can secure a sufficient close contactability with respect to the inserting member.

BRIEF DESCRIPTION OF THE DRAWINGS

FIG. 2 is a main part-exploded perspective view of the fixing structure described in FIG. 1.

FIG. 8 is a main part-exploded perspective view of the fixing structure described in FIG. 7.

EMBODIMENT FOR CARRYING OUT THE INVENTION

Figure 1:
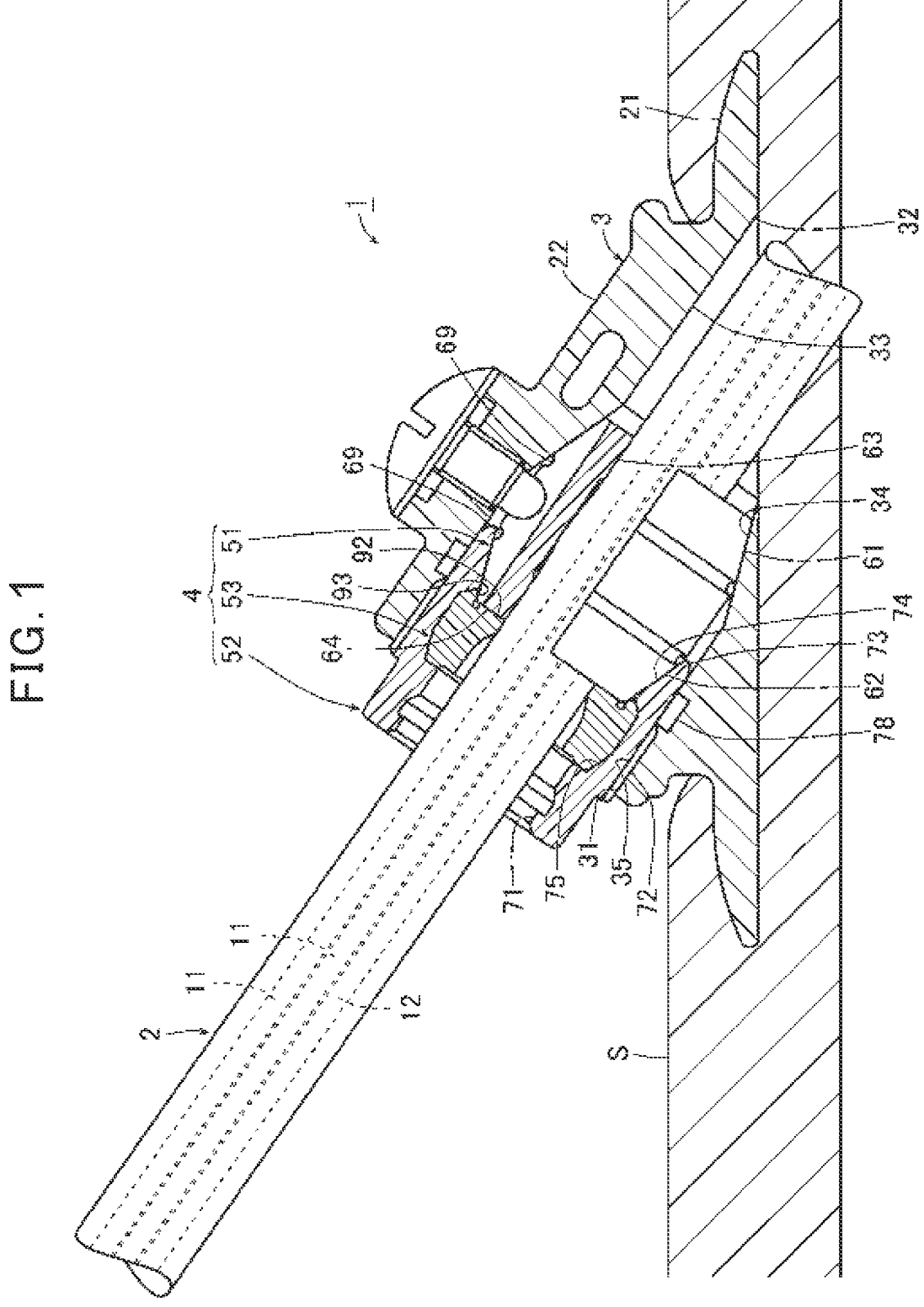
FIG. 1 is a side partial cross-sectional view of a fixing structure according to one embodiment.

Next, embodiments of the invention will be described. First, a fixing structure 1 for an inserting member according to one embodiment of the present invention will be described. In the present embodiment, one end side in the axial direction is to refer to an outer side of the body along the axial direction of the inserting member, and the other end side in the axial direction is to refer to an inner side of the body along the axial direction of the inserting member.

The fixing structure 1 according to the present embodiment is a structure to fix an inserting member to be inserted through a target. Here, "inserting" means a state in which the inserting member having a length is present at least over the interior and the exterior of the fixing structure 1. The inserting member may or may not pass through the target if a portion inserted through the target is held. The target has a hole through which the inserting member is inserted, and the inserting member is inserted through the hole.

In the present embodiment, a driveline 2 being one example of the inserting member and one type of a medical tube is guided such that the driveline 2 reaches an object site inside the body from a skin S being the target. It should be noted that the inserting member is not limited to the driveline 2, so that the inserting member may be, for example, a catheter, a different medical tube, or a solid medical cable, or may be a different member having a length. Moreover, while the target through which the inserting member is inserted may be a body cavity to which the inserting member is introduced through percutaneously, the target is not limited to the skin. The target is preferably a target into which invasion of bacteria and the like needs to be suppressed, for example, a living organism including an element constituting a living body such as an organ, a bone <Configuration of Fixing Structure>

Next, an overall configuration of the fixing structure 1 according to the present embodiment will be described using FIGS. 1 and 2.

The fixing structure 1 according to the present embodiment comprises the driveline 2 being the inserting member, a fixing member 3 fixed to the skin 5, which is the target, and having an insertion hole 33 through which the driveline 2 is inserted, and a holding mechanism 4 to hold the driveline 2 with respect to the fixing member 3. Here, the fixing member 3 is fixed to the skin S" means that the fixing member 3 is fixed to the skin S by anchoring (fixing) a part of the skin S to the surface of the fixing member 3.

The driveline 2 is a tubular-shaped member to be inserted into inside the human body, and is one type of medical tube. The outer peripheral surface (the outer surface) of the driveline 2 is covered with fiber at a portion inserted into the interior of the human body. An end of the driveline 2 inside the body is coupled to a medical device (not shown) being arranged in the body. An end of the driveline 2 on the outer side of the body is coupled to a device (not shown) being arranged outside the body. A connector portion 10 (see FIG. 4) for coupling a device (not shown) may be mounted to the end of the driveline 2 on the outer side of the body. Generally, the outer diameter of the connector portion 10 is greater than the outer diameter of the driveline 2.

In the present embodiment, the medical device arranged inside the body is an auxiliary artificial heart. The auxiliary artificial heart is a member having a pump to circulate blood in the body. The device arranged outside the body includes a pressure-feeding pump to send out cooling water to cool the above-mentioned pump and a power source to feed electric power to the pump. The driveline 2 has, in the interior thereof, a cooling water circulation path 11 to circulate cooling water between the pressure-feeding pump and the auxiliary artificial heart, and a power cable 12 to connect the power source and the pump. The configuration of the driveline 2 is not limited thereto, so that a publicly-known configuration may be adopted. For example, the driveline 2 may be configured to have only the power cable 12, may be configured to have only the cooling water circulation path 11, or may be configured to have a member having a different function.

The fixing member 3 has a fixing portion 21 to be fixed to the skin S and an insertion portion 22 through which the driveline 2 is inserted. While details will be described below, here, a surface treatment is applied to at least a part of the fixing member 3 to promote anchoring of a part of the skin S. A material for the fixing member is not particularly limited as long as the fixing member has rigidity with which the fixing member can be fixed to a target. In a case that the fixing member is a member to be fixed to the skin S being biological tissues as in the present embodiment, it is preferable that the fixing member is formed of a material having a high biocompatibility. Materials having the high biocompatibility include polyester, polyether ether ketone, silicon, titanium, and a titanium alloy, for example. The surface of the fixing portion 21 is formed with a porous material such as a mesh-shaped titanium fiber, into which porous material cells can invade, improving close contactability between the fixing portion 21 and the skin S to achieve the prevention of invasion of bacteria into the living body.

The fixing portion 21 is a portion to be fixed to the skin S being the target to be inserted through, and, in detail, is a portion to be fixed to the skin S around a hole formed in the skin S. The fixing portion 21 is provided to the outer periphery of the insertion portion 22, and the fixing portion 21 is integrally configured with the insertion portion 22. While the fixing portion 21 is integrally configured with the insertion portion 22 in the present embodiment, it is not limited thereto. For example, the fixing portion 21 being provided as a separate body may be fixed to the outer periphery of the insertion portion 22 by welding and the like.

The insertion portion 22 is a portion through which the driveline 2 is inserted and is configured in a substantially cylindrical shape. The insertion portion 22 has a first opening 31 on one end side in the axial direction, a second opening 32 on the other end side in the axial direction, an insertion hole 33 communicating the first opening 31 and the second opening 32, a fixing member-side fitted portion 34 provided such that a cross-sectional shape of the fixing member-side fitted portion 34 gradually decreases in diameter from the first opening 31 toward the second opening 32 in an intermediate portion in the axial direction of the inner surface of the insertion hole 33, and a female screw portion 35 provided to the first opening 31 being one end of the insertion hole 33 in the axial direction. In each of the drawings, illustration of the screw groove and the like of the female screw portion 35 is omitted.

The first opening 31 is an opening provided on the outer side of the body of the insertion portion 22, while the second opening 32 is an opening provided on the inner side of the body. The first opening 31 is formed such that the opening surface thereof is orthogonal with respect to the axial direction of the insertion portion 22. The second opening 32 is formed such that the opening surface thereof is non-orthogonal with respect to the axial direction of the insertion portion 22. The cross section of the first opening 31 is formed in a circular shape, and the diameter of the first opening 31 in the cross section is substantially same as the outer diameter of a screw member 52 to be described below. The cross section of the second opening 32 is formed in an elliptical shape, and the cross-sectional area of the second opening 32 is formed to be greater than the cross-sectional area of the driveline 2 when the driveline 2 is cut in a direction being parallel to the second opening 32.

The insertion hole 33 is a hole through which the driveline 2 is inserted and is formed in a cross-sectionally circular shape. The insertion hole 33 is formed in a circular shape in a cross-sectional view. The insertion hole 33 is configured such that the central axis thereof forms one straight line. While the insertion hole 33 is formed such that the central axis thereof forms one straight line, it is not limited thereto. The insertion hole 33 may be formed to be curved or bent at the intermediate portion of the insertion hole 33, for example. Moreover, in the present embodiment, the insertion hole 33 is configured to be inclined with respect to the fixing portion 21, but the inclined angle is not particularly limited. Furthermore, the insertion hole 33 may be formed to be orthogonal to the target.

The fixing member-side fitted portion 34 is a portion provided on the inner surface of the insertion hole 33 and is provided such that the inner diameter thereof is reduced toward the second opening 32 from the first opening 31. The fixing member-side fitted portion 34 is provided such that the inclined angle of the fixing member-side fitted portion 34 is constant. In other words, the fixing member-side fitted portion 34 is configured in a straight-line shape in the cross section shown in FIG. 1. While the fixing member-side fitted portion 34 is formed such that the inclined angle thereof is constant in the present embodiment, it is not limited thereto. For example, the fixing member-side fitted portion 34 may also be formed such that the inclined angle of the fixing member-side fitted portion 34 increases toward the second opening 32. In this case, the fixing member-side fitted portion is configured such that the cross section shown in FIG. 1 is in a curved shape.

The female screw portion 35 is a portion provided on the inner peripheral surface of the first opening 31. A male screw portion 72 to be described below screws into the female screw portion 35.

Moreover, a square ring 78 is arranged on the inner periphery of the insertion hole 33. The square ring 78 is provided between the inner peripheral surface of the insertion hole 33 and the outer peripheral surface of the screw member 52. The square ring 78 is a member having a role to assist in liquid-tightness between the insertion portion 22 and the screw member 52. The square ring 78 may be attached to the outer periphery of the screw member 52.

The holding mechanism 4 of the present embodiment is a mechanism to hold the driveline 2 with respect to the fixing member 3 and has a mechanism to keep the inner side of the body liquid-tight. The holding mechanism 4 comprises a chuck member 51, the screw member 52, and a sealing member 53.

The chuck member 51 is a member to tighten and grasp the inserting member such as the driveline 2, The chuck member 51 has a chuck member-side first fitting portion 61 provided on the outer peripheral surface at the other end side in the axial direction and having a shape corresponding to the fixing member-side fitted portion 34. The chuck member 51 has a chuck member-side second fitting portion 62 provided on the outer peripheral surface at one end side in the axial direction and fitted to the sealing member 53 and the screw member 52. The chuck member 51 has a grasping portion 63 provided on the inner side of the chuck member 51 and grasping tightly against the outer periphery of the driveline 2. The chuck member 51 has an end face 64 on the one end side in the axial direction, which contacts the sealing member 53.

The chuck member 51 is a member to be arranged between the inner peripheral surface of the insertion hole 33 and the outer peripheral surface of the driveline 2. The chuck member 51 has, in the holding mechanism 4, a role of grasping the driveline 2 by tightening the driveline 2 and a role of achieving liquid tightness. A material for the chuck member 51 is not particularly limited. A material capable of being slightly deformed such as to make it possible to tighten the driveline 2 may be used as a material capable of achieving the role of holding the driveline 2 and the role of achieving the liquid tightness. The chuck member 51 in the present embodiment is formed of a metal having a high corrosion resistance, which metal has the hardness equivalent to that of a metal forming the fixing member 3 or the hardness lower than that of the material forming the fixing member 3. The metal having the high corrosion resistance may be titanium or a titanium alloy, for example.

In a state where the chuck member 51 is arranged in the insertion hole 33, the chuck member-side first fitting portion 61 is a portion to fit to the fixing member-side fitted portion 34. The chuck member-side first fitting portion 61 is configured to fit to the fixing member-side fitted portion 34 such that a force in a direction in which the chuck member 51 is reduced in diameter (a force toward the driveline 2) is applied to the chuck member 51 from the fixing member-side fitted portion 34. In the present embodiment, the chuck member-side first fitting portion 61 is identical to that of the fixing member-side fitted portion 34. In other words, the chuck member-side first fitting portion 61 is configured to fit to the fixing member-side fitted portion 34 in a surface contact with the fixing member-side fitted portion 34. In other words, an inclined surface having identical inclined angle to that of fixing member-side fitted portion 34 is preferably formed in at least one portion of the chuck member-side first fitting portion 61.

While the chuck member-side first fitting portion 61 is configured by the inclined surface, it is not limited thereto. Regarding the shape of the chuck member-side first fitting portion 61, it is enough that the chuck member-side first fitting portion 61 can receive a force in a direction in which the chuck member 51 is pushed to the first opening 31 side at least from the fixing member-side fitted portion 34.

In a state where the chuck member 51 is arranged in the insertion hole 33, the chuck member-side second fitting portion 62 is a portion to fit to the sealing member 53 and the screw member 52. The chuck member-side second fitting portion 62 is configured as an inclined surface formed on the first opening 31 side of the chuck member 51. The chuck member-side second fitting portion 62 is configured to fit to a tip fitting portion 74 of the screw member 52 (described below) such that a force in the direction in which the chuck member 51 is reduced in diameter (a force toward the driveline 2) is applied to the chuck member 51 from the tip fitting portion 74.

Moreover, the tip fitting portion 74 of the screw member 52 also receives, from the chuck member-side second fitting portion 62, a force outwardly in a radial direction of the screw member 52. In the present embodiment, the chuck member-side second fitting portion 62 is configured by an inclined surface whose inclined angle is identical to that of the tip fitting portion 74 being an inclined surface. In other words, the chuck member-side second fitting portion 62 is configured to contact the tip fitting portion 74 in a surface contact with the tip fitting portion 74. In other words, an inclined surface having inclined angle identical to that of the tip fitting portion 74 is preferably formed in at least one portion of the chuck member-side second fitting portion 62.

While the chuck member-side second fitting portion 62 is configured with an inclined surface, it is not limited thereto. It suffices that the chuck member-side second fitting portion 62 has a shape capable of receiving a force from the screw member 52 in a direction in which the chuck member 51 is at least pushed toward the second opening 32 side.

The grasping portion 63 is a portion to fit to the outer periphery of the driveline 2, and in the present embodiment, the grasping portion 63 is the entire inner peripheral surface of the chuck member 51. The chuck member 51 has a communicating hole to communicate an opening at a side of the first opening 31 and an opening at a side of the second opening 32 and grasps the driveline 2 such that the driveline 2 extends out of these openings. The grasping portion 63 is formed in a circular shape in a cross section and is formed such that the diameter of the cross section of the grasping portion 63 is uniform as shown in FIG. 1. While the grasping portion 63 is formed such that the diameter of the cross section thereof is uniform, it is not limited thereto. The grasping portion 63 may have a step portion formed such that the diameter of the cross section increases in the central region of the grasping portion 63, for example.

The end face 64 is a contacting portion to contact an annular protruding portion 92 to be described below of the sealing member 53 in a state where the chuck member 51 is arranged in the insertion hole 33. The end face 64 is configured with a surface being parallel to the radial direction of the insertion portion 22 and is continuously formed with chuck member-side second fitting portion 62. While the end face 64 is configured with the surface being parallel to the radial direction of the insertion portion 22, it is not limited thereto. It suffices that the end face 64 has a shape capable of receiving a force from the annular protruding portion 92 of the sealing member 53 in a direction in which the chuck member 51 is pushed toward the second opening 32 side.

Figure 2:
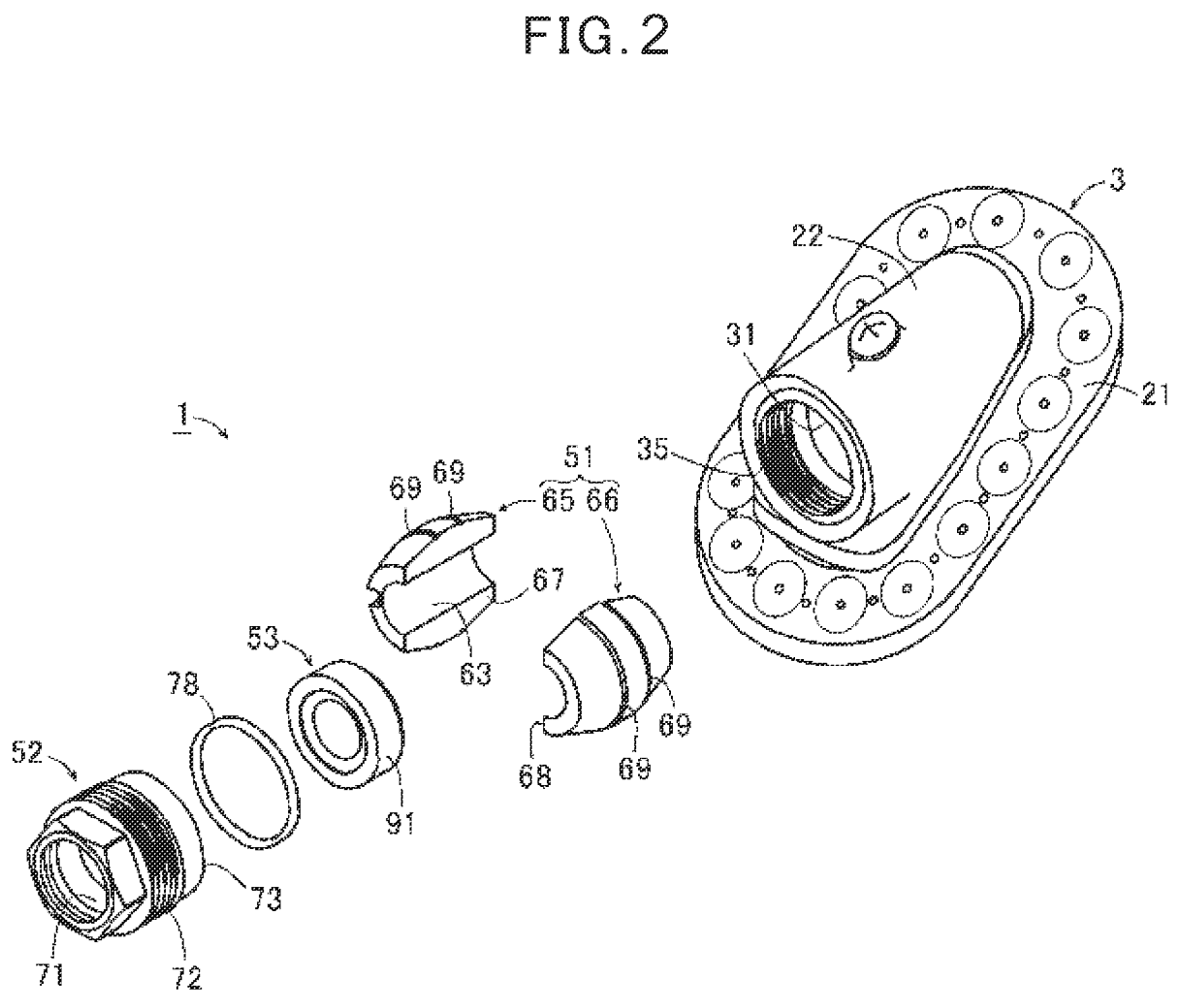

As shown in FIG. 2, the chuck member 51 in the present embodiment configured by a first chuck member 65 and a second chuck member 66. The chuck member 51 may be divided in the radial direction and may be a substantially tubular body by integrally joining the first chuck member 65 and the second chuck member 66. The chuck member 51 is formed when a joining surface 67 of the first chuck member 65 and a joining surface 68 of the second chuck member 66 are joined. Moreover, the outer peripheral surface of the chuck member 51 has a concave portion 69. The concave portion 69 is provided in order to stop sliding of the chuck member 51 when the chuck member 51 is fitted to the fixing member-side fitted portion 34 and the tip fitting portion 74. The structure of the chuck member 51 is not limited to the structure capable of being divided in the radial direction. The chuck member 51 may be configured as the structure capable of being divided in the axial direction or the structure not capable of being divided.

The screw member 52 is a member arranged on one end side in the axial direction with respect to the sealing member 53. The screw member 52 has the male screw portion 72 to be screwed into the female screw portion 35. The screw member 52 is configured to press the chuck member 51 and the sealing member 53 toward the other end side in the axial direction by screwing the male screw portion 72 into the female screw portion 35. The screw member 52 has a screw member inserting path 71 through which the driveline 2 is inserted, the male screw portion 72 provided on the outer peripheral surface, and a tip portion 73 to be inserted into the insertion portion 22. The screw member 52 has a tip fitting portion 74 provided on the inner side of the tip portion 73 to fit to the chuck member-side second fitting portion 62, and a screw member fitting portion 75 to fit to the sealing member 53.

The screw member 52 is arranged between the inner peripheral surface of the insertion hole 33 and the outer peripheral surface of the sealing member 53 and between the inner peripheral surface of the insertion hole 33 and the outer peripheral surface of the chuck member 51. The screw member 42 has, in the holding mechanism 4, a role of closing the first opening 31 and a role of pressing the chuck member 51 and the sealing member 53. A material for the screw member 52 is not particularly limited as long as the material is capable of achieving the role of closing the first opening 31 and the role of pressing the chuck member 51 and the sealing member 53. In the present embodiment, the screw member 52 is formed of a metal having a high corrosion resistance, which metal has the hardness equivalent to that of a metal forming the fixing member 3 or the hardness lower than that of the metal forming the fixing member 3. The metal having the high corrosion resistance may be titanium or a titanium alloy, for example.

The screw member inserting path 71 is a path provided inside the screw member 52 to insert the driveline 2 through the screw member 52. The screw member inserting path 71 is provided from the end at one end side in the axial direction to the intermediate portion and has a diameter being greater than the outer diameter of the connector portion 10.

The male screw portion 72 is a portion provided on the outer peripheral surface of the screw member 52 to be screwed into the female screw portion 35. The tip portion 73 is a portion to be inserted into the insertion hole 33 of the fixing member 3, and the male screw portion 72 is provided on the outer peripheral surface thereof. In each of the drawings, illustration of threads of the male screw portion 72 and the like is omitted.

The tip fitting portion 74 is a portion provided on the inner peripheral surface of the tip portion 73 to fit to the chuck member-side second fitting portion 62. The tip fitting portion 74 is configured with an inclined surface having an inclined angle being identical to the inclined angle of the inclined surface of the chuck member-side second fitting portion 62. While the tip fitting portion 74 is configured with an inclined surface having an inclined angle being identical to the inclined angle of the inclined surface of the chuck member-side second fitting portion 62, the tip fitting portion 74 is not limited thereto. It suffices that the tip fitting portion 74 has a shape capable of transmitting a force from the screw member 52 in a direction in which the chuck member 51 is pushed toward the second opening 32 by fitting at least a part of the tip fitting portion 74 to the chuck member-side second fitting portion 62.

Figure 3:
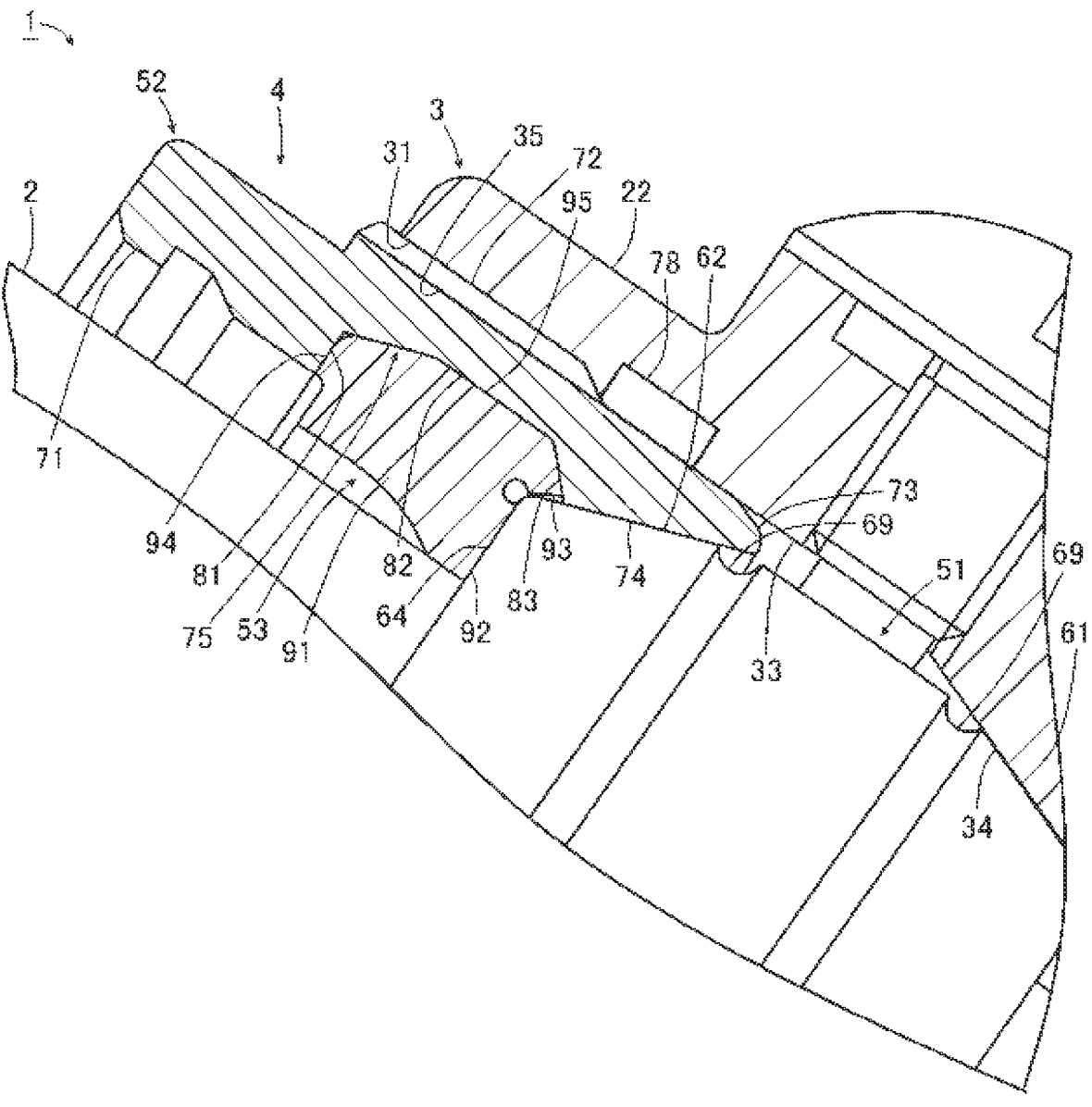
FIG. 3 is partially expanded cross-sectional view of a holding mechanism described in FIG. 1.

The screw member fitting portion 75 is a portion to fit to the sealing member 53. As shown in FIG. 3, the screw member fitting portion 75 has a pressing surface 81 provided at the first opening 31 side and being parallel to the radial direction, a contact surface 82 being parallel to the outer peripheral surface of the sealing member 53, and a contact surface 83 being provided such that the inner diameter of the contact surface 83 is reduced toward the second opening 32 side from the first opening 31 side. The configuration of the screw member fitting portion 75 is not limited to the configuration shown in the present embodiment as long as the screw member fitting portion 75 fits to the sealing member 53 and has the pressing surface 81.

The sealing member 53 is a member arranged between the inner peripheral surface of the screw member 52 and the outer surface of the driveline 2. The sealing member 53 has a role of holding the driveline 2 by tightening the driveline 2 and a role of achieving the liquid tightness in the holding mechanism 4. The sealing member 53 is configured by a cylindrical elastic member and is a member being arranged on one end side in the axial direction with respect to the chuck member 51. For the material of the sealing member 53, it is possible to use an elastic member capable of having the role of holding the driveline 2 by tightening the driveline 2 and the role of achieving the liquid tightness. The elastic member is preferably an elastic resin material, which elastic resin material includes a single synthetic resin composition such as an elastic silicone resin, and a mixture of a synthetic resin and an inorganic compound.

Figure 4:
FIG. 4 is a view describing an assembling method of the fixing structure described in FIG. 1.

The sealing member 53 has a main body portion 91, an annular protruding portion 92, and a sealing member-side fitted portion 93. The main body portion 91 is a cylindrical portion through which the driveline 2 is inserted. As shown in FIG. 4, the inner diameter of the main body portion 91 is configured to be greater than the outer diameter of the driveline 2 and to be equal to or slightly less than the outer diameter of the connector portion 10. Accordingly, it is possible to make the sealing member 53 as small as possible and to pass the sealing member 53 through the connector portion 10 with the sealing member 53 deformed. The outer peripheral surface of the main body portion 91 has a shape corresponding to the screw member fitting portion 75, and, as shown in FIG. 3, has a pressed surface 94 to be pressed by the pressing surface 81 of the screw member 52 and a contacted surface 95 to be contacted by the contacting surface 82 of the screw member 52. In this way, the main body portion 91 is fitted to the screw member 52. As a result, liquid-tightness is achieved on the outer peripheral surface of the main body portion 91.

Figure 5:
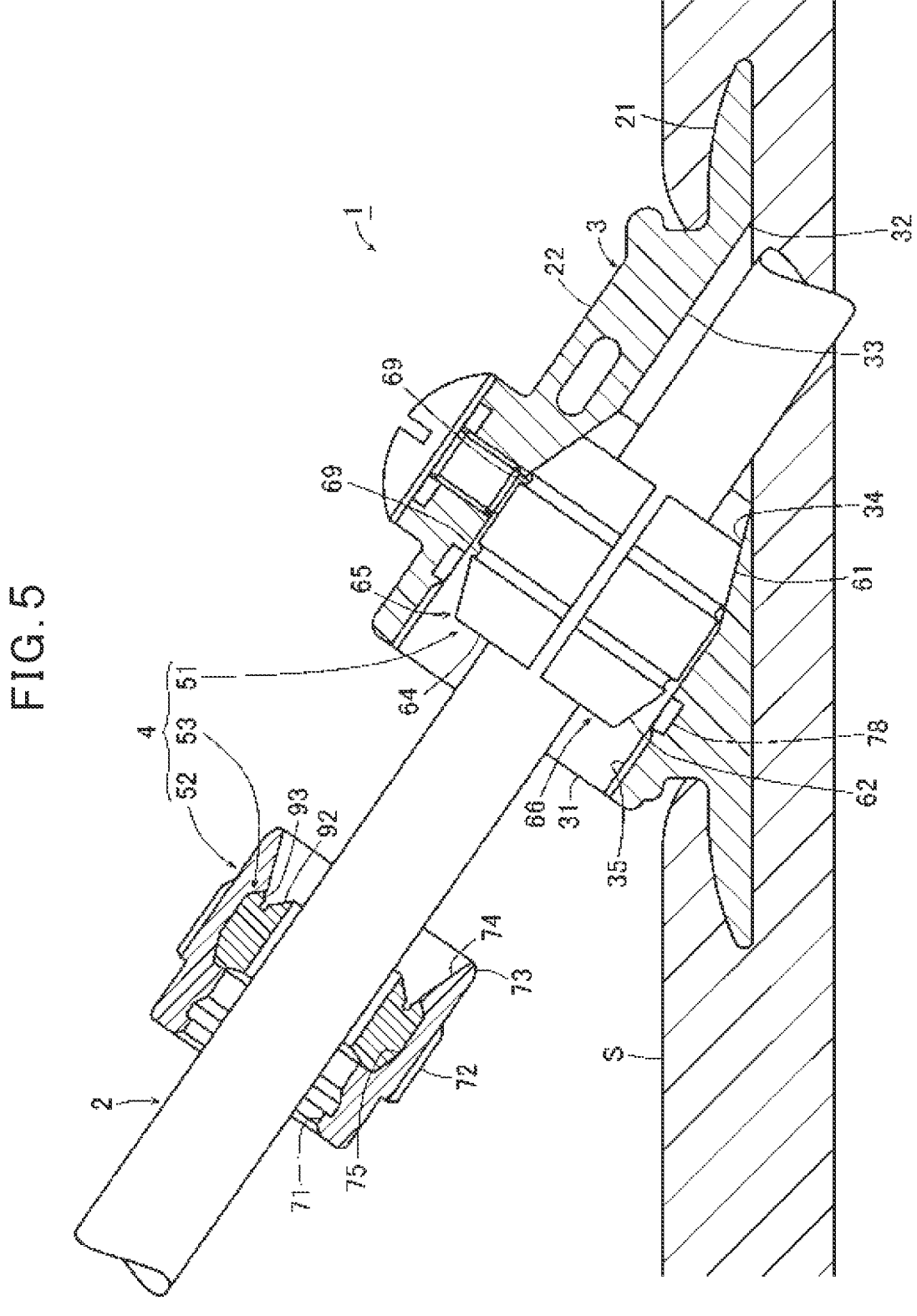
FIG. 5 is a view describing the assembling method of the fixing structure described in FIG. 1.
Figure 6:
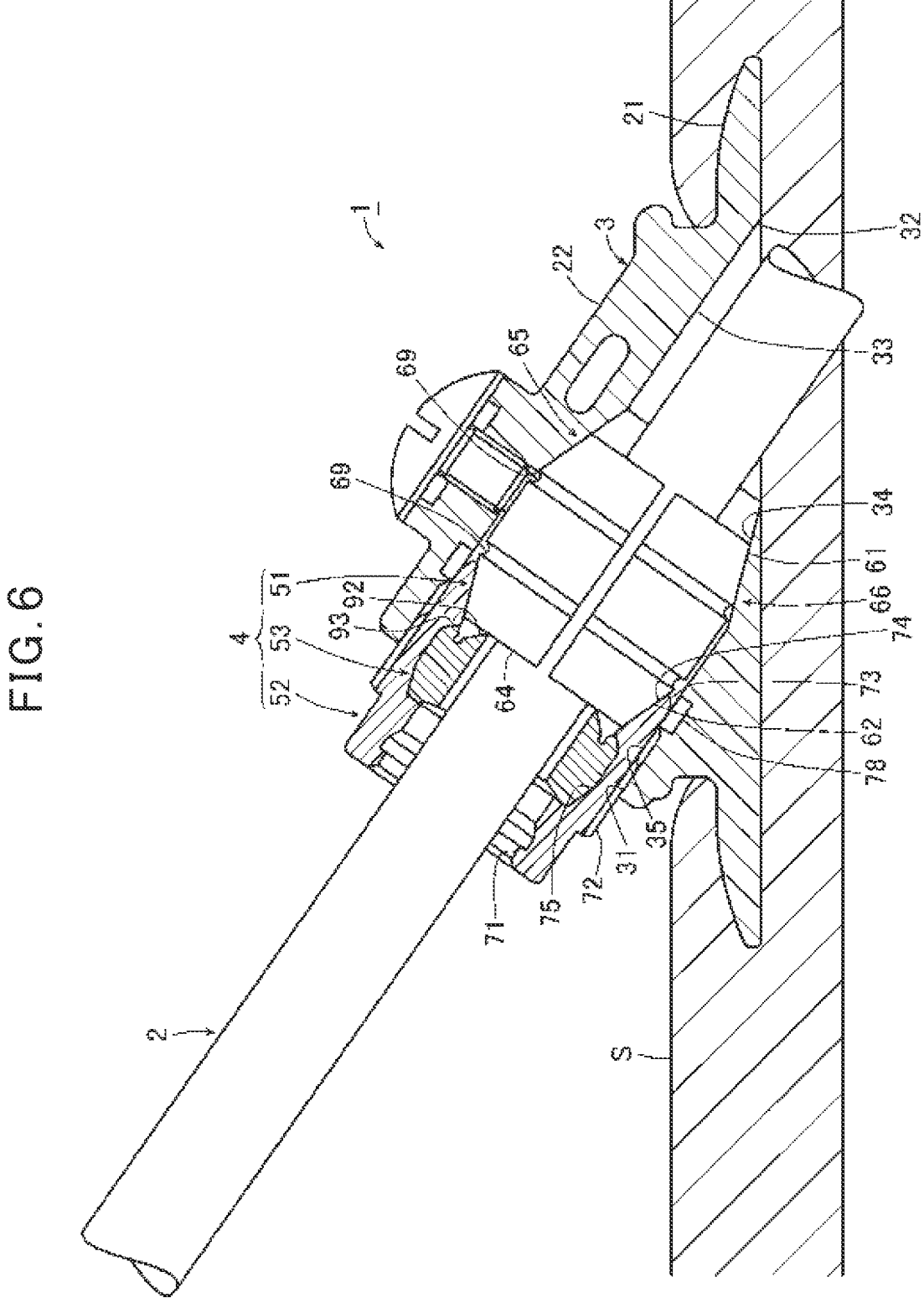
FIG. 6 is a view describing the assembling method of the fixing structure described in FIG. 1.

As shown in FIG. 5, the annular protruding portion 92 is a portion projecting toward the other end side in the axial direction from an end on the other end side of the main body portion 91, and the cross-sectional shape of the annular protruding portion 92 gradually decreases in diameter toward the projecting direction of the annular protruding portion 92. In the present embodiment, the annular protruding portion 92 is configured in a cross-sectionally triangular shape. The annular protruding portion 92 bends and deforms to the inner side of the sealing member 53 in the radial direction as shown in FIGS. 1 and 3, by contacting the annular protruding portion 92 with the end face 64 on one side of the chuck member 51 in the axial direction at the time of assembling as shown in FIG. 6. Accordingly, the inner diameter of the annular protruding portion 92 becomes less than the inner diameter of the main body portion 91 and the annular protruding portion 92 is in close contact with the end face 64 of the chuck member 51 and the outer peripheral surface of the driveline 2. Thus, the annular protruding portion 92 tightens the driveline 2 to hold the driveline 2 and achieves liquid-tightness on the inner peripheral surface of the main body portion 91.

It should be noted that the shape of the annular protruding portion 92 is not particularly limited as long as it is a shape capable of bending and deforming to the inner side of the sealing member 53 in the radial direction. Therefore, the annular protruding portion 92 may have a substantially triangular shape in cross section so as to bend to the inner side of the radial direction, for example.

As shown in FIGS. 3 and 5, the sealing member-side fitted portion 93 is an annular portion provided on the outer side of the annular protruding portion 92 in the radial direction and at least having a shape corresponding to the chuck member-side second fitting portion 62. In the present embodiment, the sealing member-side fitted portion 93 is configured to be a triangular shape in cross section corresponding to the chuck member-side second fitting portion 62 and the contacting surface 83 of the screw member 52. In this way, the sealing member-side fitted portion 93 is fitted with the sealing member-side fitted portion 93 being in close contact with the chuck member-side second fitting portion 62 and the contacting surface 83. Thus, the close contactability of the sealing member 53 with respect to the chuck member 51 and the screw member 52 can be further enhanced.

With respect to the configuration of the sealing member 53, the sealing member 53 does not need to have the sealing member-side fitted portion 93 as long as the sealing member 53 has the main body portion 91 and the annular protruding portion 92. Therefore, the configuration of the sealing member 53 is not limited to the configuration shown in the present embodiment, <Assembling of Fixing Structure>

Next, a method of assembling the fixing structure 1 will be described using FIGS. 1 to 6, As shown in FIG. 4, the driveline 2 is inserted through the insertion hole 33 of the fixing member 3. For example, the fixing member 3 can be inserted from the second opening 32 with respect to driveline 2 extending to the outer side of the body from a hole provided in the skin S.

Next, the grasping portion 63 of the second chuck member 66 is contacted with the outer periphery of the driveline 2 while contacting the grasping portion 63 of the first chuck member 65 configuring the chuck member 51 with the outer periphery of the driveline 2. By opposing the joining surface 67 of the first chuck member 65 and the joining surface 68 of the second chuck member 66, the chuck member 51 is arranged on the outer periphery of the driveline 2.

Next, as shown in FIG. 5, the chuck member 51 is inserted through the insertion hole 33 from the first opening 31 side. Here, the chuck member-side first fitting portion 61 of the chuck member 51 being inserted through the insertion hole 33 is contacting the fixing member-side fitted portion 34 of the fixing member 3, however, the chuck member-side first fitting portion 61 does not have to contact the fixing member-side fitted portion 34 at this time. Next, as shown in FIG. 4, the sealing member 53 passes through the connector portion and the sealing member 53 is fitted to the upper side (the first opening 31 side) of the chuck member 51 at the outer periphery of the driveline 2. Thereafter, the screw member 52, to which the square ring 78 is fitted, passes through the connector portion 10 and is fitted to the sealing member 53 on the outer periphery of the driveline 2.

Next, as shown in FIG. 6, the screw member 52, to which the sealing member 53 is fitted, is moved along the driveline 2, and the male screw portion 72 of the screw member 52 is screwed into the female screw portion 35 of the fixing member 3. In this way, the screw member 52 moves to the other end side of the fixing member 3 in the axial direction. Then, the tip fitting portion 74 of the screw member 52 presses the chuck member-side second fitting portion 62 of the chuck member 51. At the same time, the annular protruding portion 92 of the sealing member 53 contacts the end face 64 of the chuck member 51. At this time, in case that the chuck member-side first fitting portion 61 of the chuck member 51 does not contact the fixing member-side fitted portion 34 of the fixing member 3, the chuck member 51 moves to the other end side in the axial direction, and the chuck member-side first fitting portion 61 contacts the fixing member-side fitted portion 34.

Furthermore, as the screwing of the male screw portion 72 into the female screw portion 35 proceeds, as shown in FIG. 1, the annular protruding portion 92 of the sealing member 53 is bent and deformed to the inner side in the radial direction by the end face 64 of the chuck member 51. Therefore, the annular protruding portion 92 comes into close contact with the end face 64 of the chuck member 51 and the outer peripheral surface of the driveline 2. Then, movement of the chuck member 51 is restricted, so that mounting of the screw member 52 and the sealing member 53 to the fixing member 3 is completed and assembling of the fixing structure 1 is completed. It should be noted that the above-described assembling procedure is one example, so that a procedure of assembling up to screwing of the male screw portion 72 of the screw member 52 into the female screw portion 35 of the fixing member 3 is not particularly limited.

<Effect>

As described above, the fixing structure. 1 of the present embodiment comprises a driveline 2 to be inserted through the skin S, a fixing member 3 fixed to the skin S and having an insertion hole 33 through which the driveline 2 is inserted, and a holding mechanism 4 to hold the driveline 2 with respect to the fixing member 3. The fixing member 3 has a female screw portion 35 on one end of the insertion hole 33 in the axial direction and has a fixing member-side fitted portion 34, wherein a cross-sectional shape of the fixing member-side fitted portion 34 gradually decreases in diameter from one end side toward the other end side in an intermediate portion in the axial direction. The holding mechanism 4 comprises the chuck member 51 having a chuck member-side first fitting portion 61 having a shape corresponding to the fixing member-side fitted portion 34, wherein the chuck member 51 grasps the driveline 2 by fitting the chuck member-side first fitting portion 61 to the fixing member-side fitted portion 34 between an outer peripheral surface of the driveline 2 and an inner peripheral surface of the insertion hole, a sealing member 53 configured by a cylindrical elastic member and being arranged on one end side in the axial direction with respect to the chuck member 51, and a screw member 52 arranged on one end side in the axial direction with respect to the sealing member 53, wherein the screw member 52 has a male screw portion 72 to be screwed into the female screw portion 35, and the screw member 52 is configured to press the chuck member 51 and the sealing member 53 toward the other end side in the axial direction by screwing the male screw portion 72 into the female screw portion 35. The sealing member 53 has a main body portion 91 through which the driveline 2 is inserted, and an annular protruding portion 92 projecting toward the other end side in the axial direction from an end on the other end side of the main body portion 91, wherein a cross-sectional shape of the annular protruding portion 92 gradually decreases in diameter toward a projecting direction of the annular protruding portion 92. Then, the annular protruding portion 92 is configured to be bent and deformed to the inner side of the sealing member 53 in the radial direction by contacting the annular protruding portion 92 with an end face of the chuck member 51 on one end side in the axial direction.

According to such a configuration, in case that the connector portion having an outer diameter being sufficiently greater than an outer diameter of the driveline 2 is provided in the driveline 2, for example, the inner diameter of the sealing member 53 needs to be set to a size being sufficient to pass through the connector portion 10. Then, when the sealing member 53 is mounted to a predetermined position of the fixing structure 1 the annular protruding portion 92 is bent and deformed to the inner side of the sealing member 53 in the radial direction and is brought into dose contact with the outer peripheral surface of the driveline 2.

Thus, a fixing structure for the driveline 2 has the sealing member 53 that can easily pass through the connector portion 10 provided to the driveline 2 and having an outer diameter being sufficiently greater than an outer diameter of the driveline 2, and that can secure a sufficient close contactability with respect to the driveline 2. Therefore, it is possible to realize the fixing structure compactly without separately providing a complex and large-scale structure.

Moreover, in the fixing structure 1 of the present embodiment, the chuck member 51 has the chuck member-side second fitting portion 62 at an end on the sealing member 53 side, and a crass-sectional shape of the chuck member-side second fitting portion 62 gradually decreases in diameter toward one end side from the other end side in the axial direction. The sealing member 53 has an annular sealing member-side fitted portion 93 provided on the outer side of the annular protruding portion 92 in the radial direction and the annular sealing member-side fitted portion has a shape corresponding to the chuck member-side second fitting portion 62.

By such a configuration, the chuck member-side second fitting portion 62 of the chuck member 51 and the sealing member-side fitted portion 93 of the sealing member 53 are fitted to each other with the chuck member-side second fitting portion 62 of the chuck member 51 and the sealing member-side fitted portion 93 of the sealing member 53 being in close contact with each other. Thus, the close contactability of the sealing member 53 with respect to the chuck member 51 can be further enhanced.

Moreover, the inserting member is a medical tube, which is driveline 2 in the fixing structure 1 of the present embodiment.

By such a configuration, in case that the inserting member is the medical tube, a fixing structure for the medical tube has the sealing member 53 that can easily pass through the connector portion 10 provided to the medical tube and having an outer diameter being sufficiently greater than an outer diameter of the medical tube, and that can secure a sufficient dose contactability with respect to the medical tube. Therefore, it is possible to realize the fixing structure compactly without separately providing a complex and large-scale structure.

<Variation>

Figure 7:
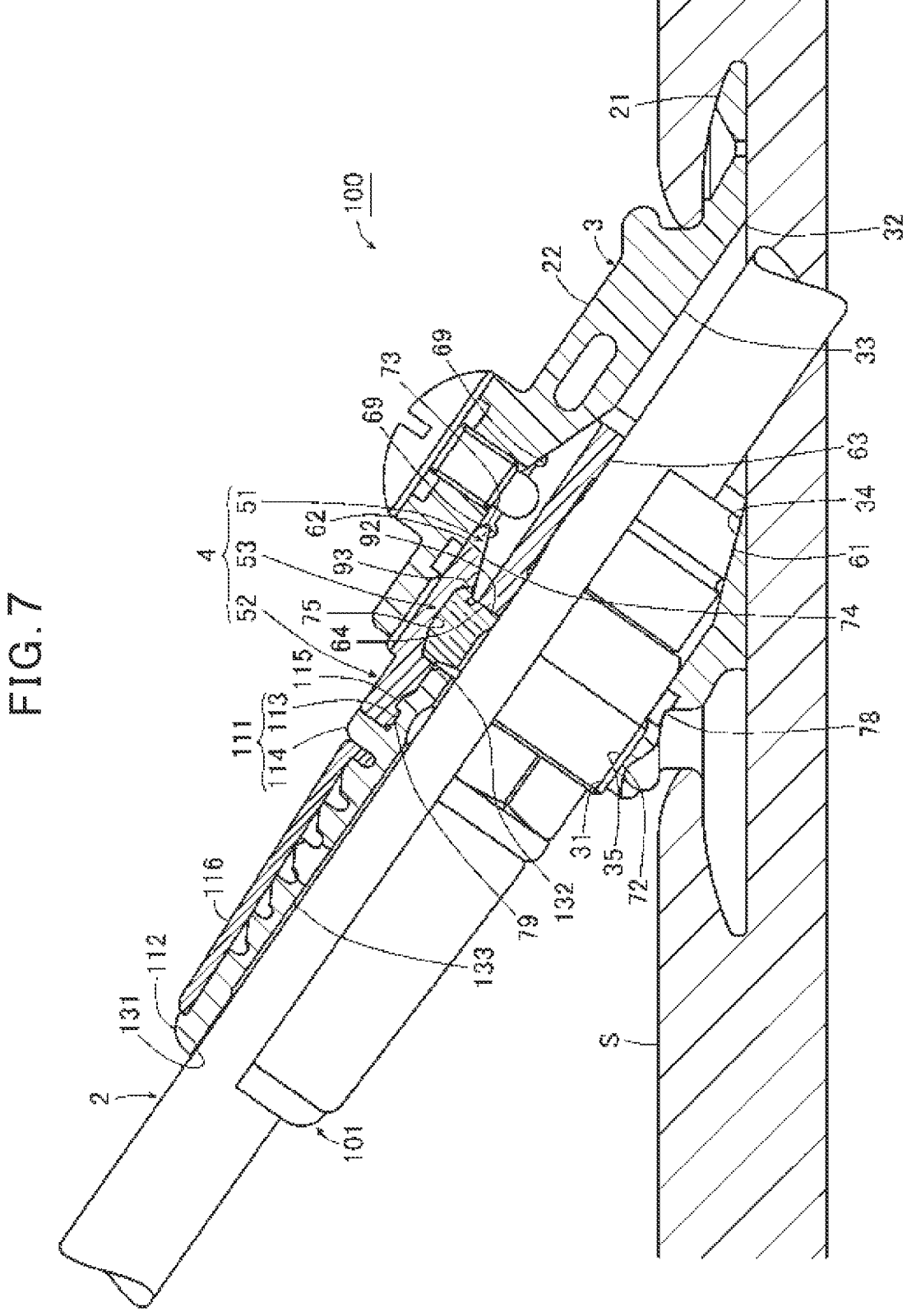
FIG. 7 is a side partial cross-sectional view of the fixing structure according to a variation.
Figure 8:
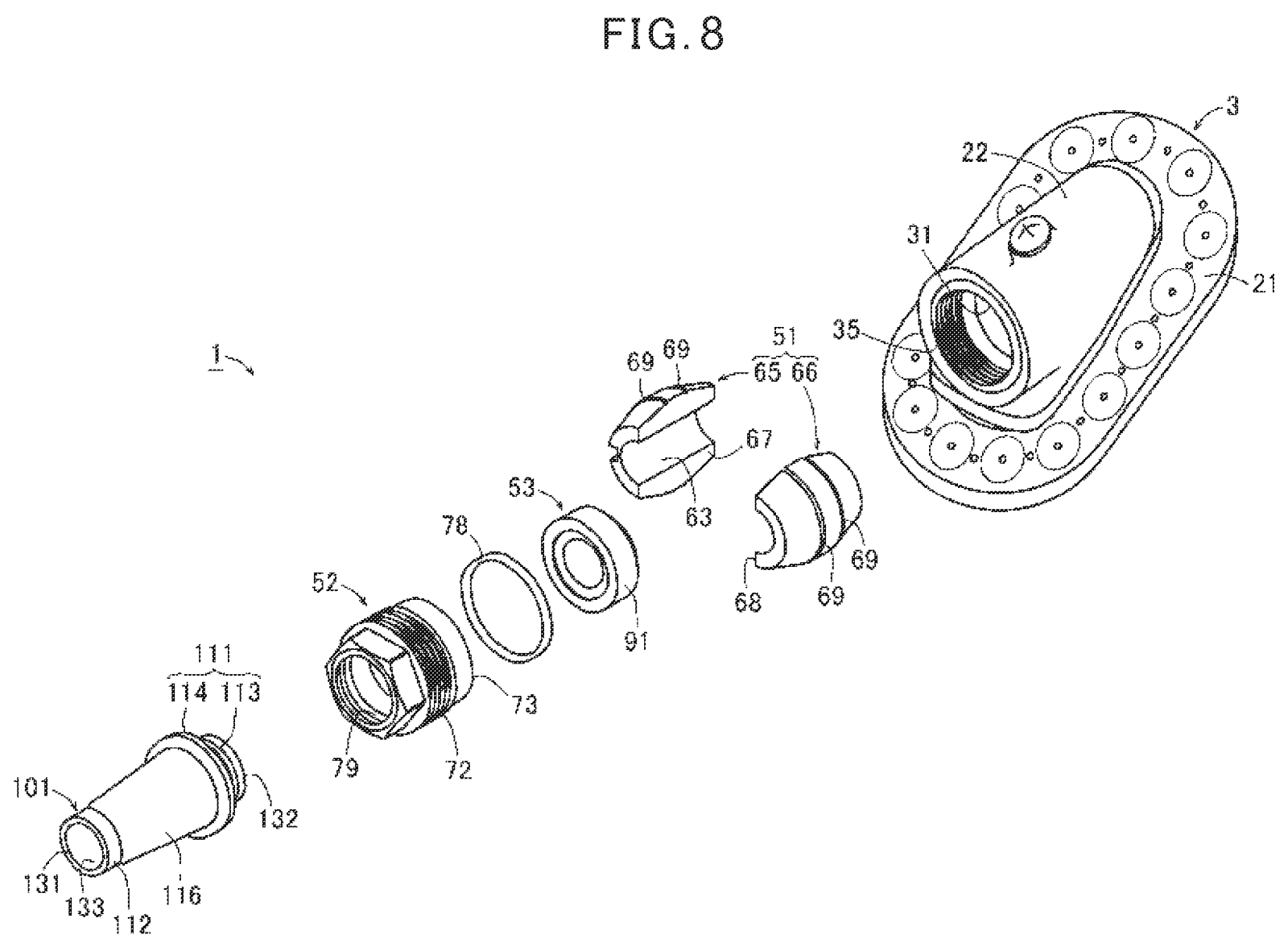

A variation of the fixing structure of the present invention will be described using FIGS. 7 and 8. The main difference between a fixing structure 100 of the variation and the above-described fixing structure 1 is that a kink guard 101 being a member to prevent bending, and torsion in the radial direction of the driveline 2 is provided at an end of the screw member 52 on the outer side of the body. The other points are the same as for the fixing structure 1 according to the above-described embodiment, so that explanations thereof will be omitted and the kink guard 101 will be described below.

The kink guard 101 has a fixing portion 111 to be fixed to the screw member 52 and a insertion portion 112 through which the driveline 2 is inserted. While the fixing portion 111 is made of silicon in the embodiment of the present variation, the material of the fixing portion 111 is not particularly limited. For example, the fixing portion 111 may be made of a hard synthetic resin. Moreover, in the embodiment of the present variation, a part of the outer peripheral surface of the kink guard 101 is covered by a cover member 116.

The fixing portion 111 is a member to be fixed to the screw member 52 and has a fitting portion 113 to be fitted to the screw member 52 and a flange portion 114 having substantially the same diameter as that of an end of the screw member 52 on one end side in the axial direction. A fitting hole 79 for fitting the fitting portion 113 of the kink guard 101 is provided at an end of the screw member 52 on one end side in the axial direction. A claw portion 115 projecting in the radial direction is provided on the outer peripheral surface of the fitting portion 113. By engaging the claw portion 115 in a concave portion provided in the fitting hole 79, the kink guard 101 is fixed to the screw member 52. In the present variation, since the claw portion 115 enters into the fitting hole 79 so as to cover the end face of the sealing member 53, it is possible to protect the sealing member 53 from the exterior.

The insertion portion 112 is a member through which the driveline 2 is inserted and is configured to be in a substantially cylindrical shape. The insertion portion 112 has a first opening 131, a second opening 132, and an insertion hole 133 communicating the first opening 131 and the second opening 132. The first opening 131 is configured to be smaller than the second opening 132, and the hole diameter of the first opening 131 is configured to be substantially identical to the outer diameter of the driveline 2, Moreover, the insertion hole 133 is formed so that the inner diameter of the insertion hole 133 increases from the first opening 131 side toward the second opening 132 side. The driveline 2 inserted through the kink guard 101 is grasped by the first opening 131, making it difficult for torsion in the radial direction, or bending of the driveline 2 to occur.

A notch may be formed from the end on the first opening 131 side to the end on the second opening 132 side on the side surface of the insertion portion 112. In this case, the kink guard 101 can be attached from the radial direction of the driveline 2 while expanding the kink guard 101. Moreover, a part or all of the outer peripheral surface of the kink guard 101 can be covered with the cover member 116 to prevent the notch of the kink guard 101 being opened. Therefore, the kink guard 101 can be replaced outside the body even after the fixing structure 1 is formed in the skin S, resulting in excellent maintainability.

As described above, in the present variation, it is possible to prevent torsion in the radial direction, and bending of the driveline 2 being a long member. It should be noted that the configuration of the kink guard 101 is not particularly limited to the above-described configuration, so that a publicly-known configuration can be applied. Moreover, the configuration having kink guard 101 can be applied to other fixing structure having a flexible inserting member, not limited to cases where the inserting member is a medical tube.

INDUSTRIAL APPLICABILITY

A fixing structure for an inserting member of the present invention is not limited to the above-described embodiments, so that it can be applied in a structure to insert an inserting member to a base body and fix the inserting member to the base body, for example. For example, other examples of the inserting member include a flexible member such as an electrical wire, a control cable, and the like, or a member having rigidity, such as a pipe arrangement. Moreover, the base body is not particularly limited, and examples thereof include a vehicular body or a wall, for example. In short, a fixing structure for an inserting member of the present invention can be used to fix the inserting member in a liquid-tight or air-tight manner.

REFERENCE SIGNS LIST

1 FIXING STRUCTURE
2 DRIVELINE (INSERTING MEMBER)
3 FIXING MEMBER
4 HOLDING MECHANISM
33 INSERTION HOLE
34 FIXING MEMBER-SIDE FITTED PORTION
35 FEMALE SCREW PORTION
51 CHUCK MEMBER
52 SCREW MEMBER
53 SEALING MEMBER
61 CHUCK MEMBER-SIDE FIRST FITTING PORTION
62 CHUCK MEMBER-SIDE SECOND FITTING PORTION
72 MALE SCREW PORTION
91 MAIN BODY PORTION
92 ANNULAR PROTRUDING PORTION
93 SEALING MEMBER-SIDE FITTED PORTION
S SKIN (TARGET)

The invention claimed is:
1. A fixing structure for an inserting member, comprising:
the inserting member to be inserted through a target;
a fixing member configured to be fixed to the target and having an insertion hole through which the inserting member is inserted; and a holding mechanism to hold the inserting member with respect to the fixing member, wherein the fixing member has a female screw portion on one end of the insertion hole in an axial direction and has a fixing member-side fitted portion, wherein a cross-sectional shape of the fixing member-side fitted portion gradually decreases in diameter from one end side toward an other end side in an intermediate portion of the fixing member in the axial direction, the holding mechanism comprises:

a chuck member having a chuck member-side first fitting portion having a shape corresponding to the fixing member-side fitted portion, wherein the chuck member grasps the inserting member by fitting the chuck member-side first fitting portion to the fixing member-side fitted portion between an outer peripheral surface of the inserting member and an inner peripheral surface of the insertion hole, a sealing member configured by a cylindrical elastic member and being arranged on one end side in the axial direction with respect to the chuck member, and a screw member arranged on one end side in the axial direction with respect to the sealing member, wherein the screw member has a male screw portion to be screwed into the female screw portion, and the screw member is configured to press the chuck member and the sealing member toward the other end side in the axial direction by screwing the male screw portion into the female screw portion;

the sealing member has a main body portion through which the inserting member is inserted, and an annular protruding portion projecting toward the other end side in the axial direction from an end on an other end side of the main body portion, wherein a cross-sectional shape of the annular protruding portion gradually decreases in diameter toward a projecting direction of the annular protruding portion, the annular protruding portion is provided at a position where the annular protruding portion contacts an end face of the chuck member on one end side in the axial direction when the screw member moves to the other end side in the axial direction so that the annular protruding portion is bent and deformed to the inner side of the sealing member in a radial direction by contacting the annular protruding portion with the end face of the chuck member on one end side in the axial direction.

2. The fixing structure for an inserting member according to claim 1, wherein the chuck member has a chuck member-side second fitting portion at an end on the sealing member side, wherein a cross-sectional shape of the chuck member-side second fitting portion gradually decreases in diameter toward one end side from the other end side in the axial direction; and the sealing member has an annular sealing member-side fitted portion provided on the outer side of the annular protruding portion in the radial direction wherein the annular sealing member-side fitted portion has a shape corresponding to the chuck member-side second fitting portion.

3. The fixing structure for an inserting member according to claim 1, wherein the inserting member is a medical tube.

4. A fixing structure for an inserting member, comprising:

the inserting member to be inserted through a target;

a fixing member configured to be fixed to the target and having an insertion hole through which the inserting member is inserted; and a holding mechanism to hold the inserting member with respect to the fixing member, wherein the fixing member has a female screw portion on one end of the insertion hole in an axial direction and has a fixing member-side fitted portion, wherein a cross-sectional shape of the fixing member-side fitted portion gradually decreases in diameter from one end side toward an other end side in an intermediate portion of the fixing member in the axial direction, the holding mechanism comprises:

a chuck member having a chuck member-side first fitting portion having a shape corresponding to the fixing member-side fitted portion, wherein the chuck member grasps the inserting member by fitting the chuck member-side first fitting portion to the fixing member-side fitted portion between an outer peripheral surface of the inserting member and an inner peripheral surface of the insertion hole, a sealing member configured by a cylindrical elastic member and being arranged on one end side in the axial direction with respect to the chuck member, and a screw member arranged on one end side in the axial direction with respect to the sealing member, wherein the screw member has a male screw portion to be screwed into the female screw portion, and the screw member is configured to press the chuck member and the sealing member toward the other end side in the axial direction by screwing the male screw portion into the female screw portion;

the sealing member has a main body portion through which the inserting member is inserted, and an annular protruding portion projecting toward the other end side in the axial direction from an end on an other end side of the main body portion, wherein a cross-sectional shape of the annular protruding portion gradually decreases in diameter toward a projecting direction of the annular protruding portion, the annular protruding portion is configured to be bent and deformed to the inner side of the sealing member in a radial direction by contacting the annular protruding portion with the end face of the chuck member on one end side in the axial direction;

wherein the chuck member has a chuck member-side second fitting portion at an end on the sealing member side, wherein a cross-sectional shape of the chuck member-side second fitting portion gradually decreases in diameter toward one end side from the other end side in the axial direction; and the sealing member has an annular sealing member-side fitted portion provided on the outer side of the annular protruding portion in the radial direction wherein the annular sealing member-side fitted portion has a shape corresponding to the chuck member-side second fitting portion.

* * * * *